(12) United States Patent
Sugiyama et al.

(10) Patent No.: US 8,021,887 B2
(45) Date of Patent: Sep. 20, 2011

(54) METHOD OF MEASURING GLYCATED HEMOGLOBIN CONCENTRATION

(75) Inventors: Koji Sugiyama, Kyoto (JP); Toshikatsu Sakai, Kyoto (JP)

(73) Assignee: Arkray, Inc., Kyoto (JP)

( * ) Notice: Subject to any disclaimer, the term of this patent is extended or adjusted under 35 U.S.C. 154(b) by 7 days.

(21) Appl. No.: 12/225,526

(22) PCT Filed: Mar. 23, 2007

(86) PCT No.: PCT/JP2007/056111
§ 371 (c)(1),
(2), (4) Date: Aug. 6, 2009

(87) PCT Pub. No.: WO2007/111283
PCT Pub. Date: Oct. 4, 2007

(65) Prior Publication Data
US 2009/0317912 A1 Dec. 24, 2009

(30) Foreign Application Priority Data
Mar. 24, 2006 (JP) .................. 2006-082101

(51) Int. Cl.
*G01N 33/72* (2006.01)
*G01N 21/63* (2006.01)
*G01N 21/01* (2006.01)

(52) U.S. Cl. .............. 436/67; 436/63; 436/66; 436/161; 436/164; 436/174; 422/70; 422/82.05; 422/82.09

(58) Field of Classification Search ..................... 436/63, 436/66, 67, 161, 164, 174; 422/68.1, 70, 422/73, 82.05, 82.09
See application file for complete search history.

(56) References Cited

U.S. PATENT DOCUMENTS

| | | | | |
|---|---|---|---|---|
| 5,543,315 A | * | 8/1996 | Sugiyama et al. | ............ 436/161 |
| 5,833,602 A | * | 11/1998 | Osemwota | ..................... 600/310 |
| 6,714,805 B2 | * | 3/2004 | Jeon et al. | ..................... 600/323 |
| 2005/0176133 A1 | * | 8/2005 | Miyashita et al. | ......... 435/287.1 |

FOREIGN PATENT DOCUMENTS

JP 2001-74748 * 3/2001

OTHER PUBLICATIONS

Hoxter. Clinical Chemistry, vol. 25, No. 1, 1979, pp. 143-146.*
Office Action from State Intellectual Property Office of People's Republic of China dated Apr. 13, 2010, for patent application No. 200780018789.1.
Munan Wang, et al., "Study of Effect of Temperature on Glycosylated Hemoglobin' Colorimetry Assay", Chinese Journal of Endoctrinology and Metabolism, 14(2), p. 98, Feb. 1987.
Jun Zhao, et al., "Measurement of Muscle Energy Metabolism by MRS and Frequency-Domain NIR Spectroscopy", Spectroscopy and Spectral Analysis, 25(6), p. 861-865, Jun. 2005.

* cited by examiner

*Primary Examiner* — Maureen M Wallenhorst
(74) *Attorney, Agent, or Firm* — Rader, Fishman & Grauer PLLC

(57) ABSTRACT

The present invention relates to a method and an apparatus that measure the concentration of glycated hemoglobin by an optical technique. A wavelength in which the molecular extinction coefficient of oxyhemoglobin agrees or substantially agrees with the molecular extinction coefficient of deoxyhemoglobin is adopted as a measurement wavelength. Preferably, the measurement wavelength is set at from 417 to 421 nm. In the present invention, the concentration of glycated hemoglobin is measured by making use of column chromatography and of using a sample prepared from red blood cells in blood.

11 Claims, 10 Drawing Sheets

FIG. 8
FIG.8A
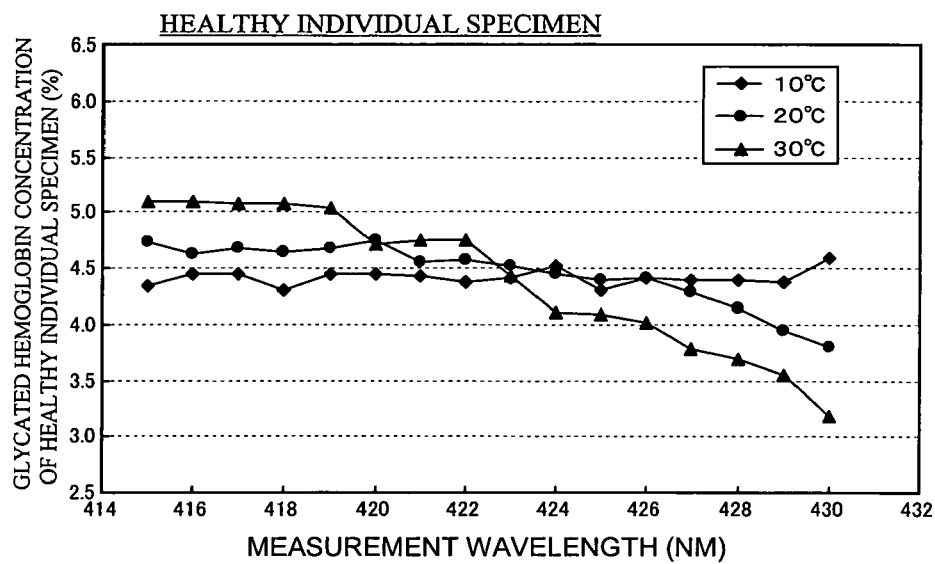
FIG.8B
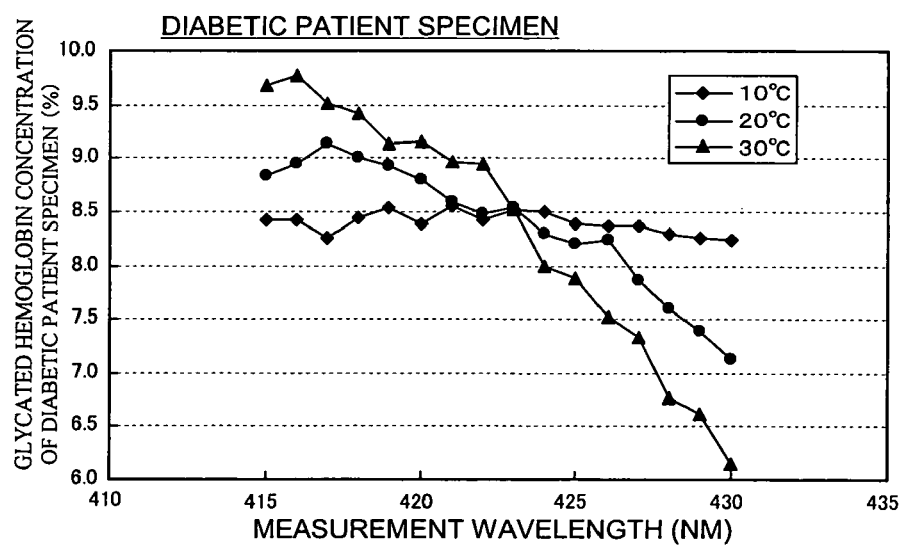

FIG. 9
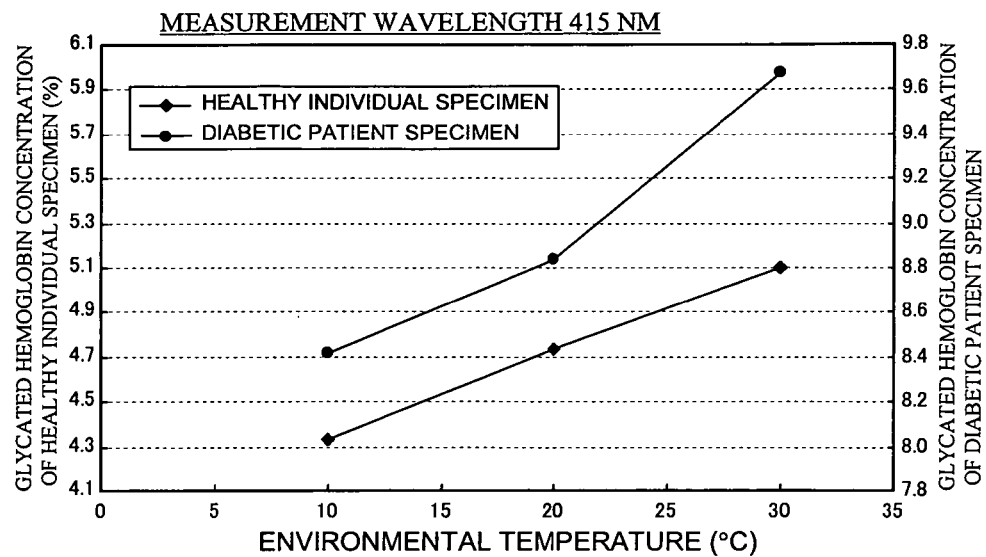
FIG.9A
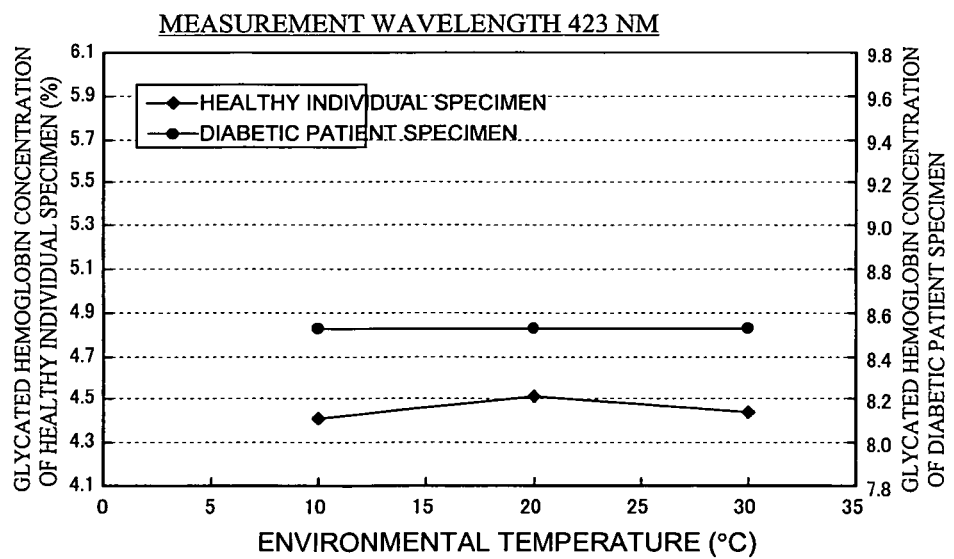
FIG.9B

US 8,021,887 B2

METHOD OF MEASURING GLYCATED HEMOGLOBIN CONCENTRATION

TECHNICAL FIELD

The present invention relates to a technique that measures the concentration of glycated hemoglobin contained in a sample of blood or the like.

BACKGROUND ART

When biological components are separated and analyzed by use of biological samples of blood or the like, high-performance liquid chromatography apparatus (HPLC apparatus) using high performance liquid chromatography (HPLC) are widely used (e.g., refer to Patent Document 1).

As shown in FIG. 10, a general HPLC apparatus 9 is configured to prepare a sample containing biological components in a sample preparation unit 90 and then to introduce the sample into an analytical column 91 to thereby adsorb the biological components to a filler of the analytical column 91. When glycated hemoglobin is measured by using whole blood as a sample, red blood cells collected from whole blood are hemolyzed and then a biological sample in a state in which the laked blood is diluted is introduced into the analytical column 91. On the other hand, a biological component adsorbed on a filler is eluted by supplying an eluent from an eluent bottle 93 to the analytical column 91 by a liquid feed pump 92. An eluent from the analytical column 91 is introduced into a photometry mechanism 94, where a biological component is analyzed by continuously measuring the absorbance of the eluent.

As shown in FIG. 11, the photometry mechanism 94 radiates light from a light source 97 while the eluent flows through a path 96 of a photometry cell 95 and receives a transmitted beam at that time in a light receiving section 98. The wavelength of light received in a light receiving section 98 is selected in an interference filter 99, while a signal of an output level corresponding to the amount of light received is output from the light receiving section 98.

The HPLC apparatus 9 further calculates the total amount of hemoglobin based on a chromatogram that is a change with the lapse of time of absorbance and also calculates the glycated hemoglobin concentration as a proportion occupied by the amount of glycated hemoglobin in the total amount of hemoglobin.

However, the amount of dissolution in an eluent of a gas such as oxygen varies depending on the temperature of the eluent. Therefore, when the temperature (environmental temperature) outside the apparatus varies or the biological component is analyzed in a state at a different environmental temperature, the state of a dissolved gas in an eluent (amount of dissolution) is different. Hence, when the dissolved oxygen concentration in an eluent varies along with the variation of environmental temperature, or the like, the ratio of the amounts of oxyhemoglobin and deoxyhemoglobin in hemoglobin varies. In addition, even in a biological sample introduced into the analytical column 91, the ratio of the amounts of oxyhemoglobin and deoxyhemoglobin in hemoglobin can vary.

On the other hand, a sample is used that has a relatively large amount of oxygen by dilution of laked blood, as a biological sample introduced into the analytical column 91, and therefore 415 nm that is the maximum absorption wavelength of oxyhemoglobin is adopted as a measurement wavelength in the photometry mechanism 94. Thus, under environments in which the change in environmental temperature is large, or the like, the ratios of the amounts of oxyhemoglobin and deoxyhemoglobin vary, whereby precise measurements become difficult when they are measured at the same wavelength.

Patent Document 1: Japanese Patent Laid-Open No. 7-120447

DISCLOSURE OF THE INVENTION

Problems to be Solved by the Invention

An object of the present invention is to be able to appropriately measure the concentration of glycated hemoglobin even when the ratio of amounts of oxyhemoglobin and deoxyhemoglobin is different.

Means for Solving the Problem

In a first aspect of the present invention, provided is a method of measuring the concentration of glycated hemoglobin by an optical technique, wherein the measurement wavelength is set at a wavelength in which the molecular extinction coefficient of oxyhemoglobin agrees or substantially agrees with that of deoxyhemoglobin.

Preferably, the measurement wavelength is set at from 417 to 427 nm. More preferably, the measurement wavelength is set at from 419 to 425 nm. As a matter of course, the measurement wavelength is not limited to the previous range and may be set at a wavelength of other wavelength ranges in which the molecular extinction coefficient of oxyhemoglobin agrees or substantially agrees with that of deoxyhemoglobin, for example, at from 520 to 526 nm or at from 583 to 589 nm.

The present invention can be applied to measurement of the concentration of glycated hemoglobin by making use of column chromatography and of using a sample prepared from red blood cells in blood.

In a second aspect of the present invention, provided is an apparatus of measuring the concentration of glycated hemoglobin including a photometry mechanism in which a sample is irradiated with light from a light source and at the time a light sensing portion receives light that travels from the sample, wherein the above photometry mechanism is configured to be capable of receiving light of a wavelength in which the molecular extinction coefficient of oxyhemoglobin agrees or substantially agrees with that of deoxyhemoglobin in the light receiving section.

The photometry mechanism is configured to be able to receive, for example, light of 417 to 427 nm in the above light receiving section. Preferably, the photometry mechanism is configured to be able to receive light of 419 to 425 nm in a light receiving section. The photometry mechanism may be configured to be able to receive light of from 520 to 526 nm or from 583 to 589 nm in a light receiving section.

The apparatus of measuring the concentration of glycated hemoglobin of the present invention further includes, for example, a separation unit for separating glycated hemoglobin making use of column chromatography.

The apparatus of measuring the concentration of glycated hemoglobin of the present invention may further include a sample preparation mechanism for preparing a sample from a red blood cell in blood.

BRIEF DESCRIPTION OF THE DRAWINGS

FIGS. 8A and 8B are graphs indicating a relationship between the environmental temperature and the concentration of glycated hemoglobin in Example 1.

FIGS. 9A and 9B are graphs indicating a relationship between the environmental temperature and the concentration of glycated hemoglobin in Example 2.

EXPLANATION OF SYMBOLS

1: Apparatus of measuring the concentration of glycated hemoglobin
3: Sample preparation unit
5: Photometry mechanism
53B: Light receiving element (light receiving section).

BEST MODE FOR CARRYING OUT THE INVENTION

Hereinafter, the present invention will be specifically described with reference to the drawings.

Figure 1:
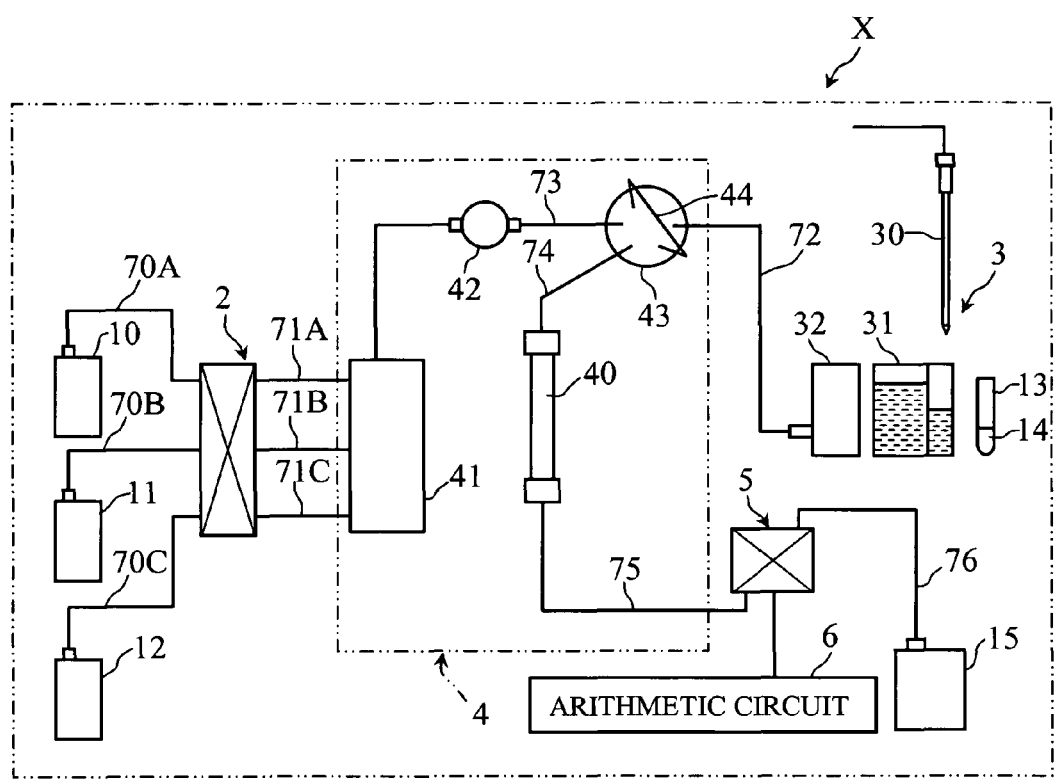
FIG. 1 is a schematic block diagram showing an HPLC apparatus that is one example of a glycated hemoglobin measuring apparatus of the present invention.

HPLC apparatus X shown in FIG. 1 corresponds to one example of the glycated hemoglobin concentration measuring apparatus of the present invention. This apparatus is configured to measure the concentration of glycated hemoglobin by use of whole blood. This HPLC apparatus X includes a plurality of eluent bottles 10, 11, and 12 (three bottles in the figure), a deaerator 2, a sample preparation unit 3, an analysis unit 4, a photometry mechanism 5, and an arithmetic circuits 6.

Each of the eluent bottles 10, 11, 12 keeps an eluent that is to be supplied to an analytical column 40 described below. Eluents make use of buffers different in, for example, pH or salt concentration.

The deaerator 2 removes a dissolved gas from an eluent prior to supplying the eluent to the analysis unit 4 (analytical column 40) and is connected to the eluent bottles 10, 11, 12 through lay pipes 70A, 70B, 70C and to a manifold 41 of the analysis unit 4 via lay pipes 71A, 71B, 71C.

As shown in FIG. 1, the sample preparation unit 3 prepares a sample that is introduced into the analytical column 40 from blood cell components of a blood sample 14 collected from a blood collection tube 13. This sample preparation unit 3 has a sampling nozzle 30, a preparation tank 31 and a dilution bath 32.

The sampling nozzle 30 collects a variety of liquids including a blood sample 14 of the blood collection tube 13, is capable of the aspiration and the discharge of a liquid and also is movable vertically and horizontally. The operation of this sampling nozzle 30 is controlled by a control unit (not illustrated).

The preparation tank 31 keeps a preparation for preparing a sample for introduction introduced into the analytical column 40 based on the blood sample 14. This preparation tank 31 keeps as a preparation laked blood for hemolyzing a red blood cell, a diluting fluid for diluting laked blood, or the like.

The dilution bath 32 provides a place for hemolyzing a red blood cell in the blood sample 14 and dilute laked blood to prepare a sample for introduction. This dilution bath 32 is connected to an injection valve 43 in the analysis unit 4 described below through piping 72 and configured to be able to introduce a sample for introduction prepared in the dilution bath 32 into the analytical column 40 through the injection valve 43.

The analysis unit 4 controls the adsorption and elution of a biological component to the filler of the analytical column 40 and supplies various biological components to the photometry mechanism 5, and is temperature controlled by a temperature control mechanism (not illustrated). The temperature in the analysis unit 4 is set, for example, at about 40° C. The analytical column 40 keeps a filler for selectively adsorb hemoglobin in a sample. A methacrylate copolymer is used, for example, as a filler.

The analysis unit 4 has a manifold 41, the liquid feed pump 42, and the injection valve 43 in addition to the analytical column 40.

The manifold 41 selectively supplies an eluent from specific eluent bottles 10, 11, 12 of a plurality of eluent bottles 10, 11, 12, to the injection valve 43. This manifold 41 is connected to the deaerator 2 through the lay pipes 71A, 71B, 71C, and connected to the injection valve 43 through piping 73.

The liquid feed pump 42 imparts a power to move an eluent to the analytical column 40 through the injection valve 43 and is provided on the way of piping 73. The liquid feed pump 42 is operated so that the flow rate of an eluent may become, for example, from 1.0 to 2.0 ml/min.

The injection valve 43 can collect the sample for introduction of a given quantity and introduce the sample for introduction into the analytical column 40, and includes a plurality of introduction ports and exhaust ports (their illustrations are omitted). An injection loop 44 is connected to this injection valve 43. This injection loop 44 can keep a liquid of a given quantity (e.g., several μL), and can select a state in which the injection valve 43 is accordingly switched to thereby communicate the injection loop 44 with the dilution bath 32 and supply a sample for introduction from the dilution bath 32 to the injection loop 44, a state in which the injection loop 44 is communicated with the analytical column 40 via piping 74 to introduce a sample for introduction from the injection loop 44 to the analytical column 40, or a state in which a cleaning solution is supplied to the injection loop 44 from a cleaning tank (not illustrated). As such an injection valve 43, for example, a hexagonal valve can be used.

Figure 2:
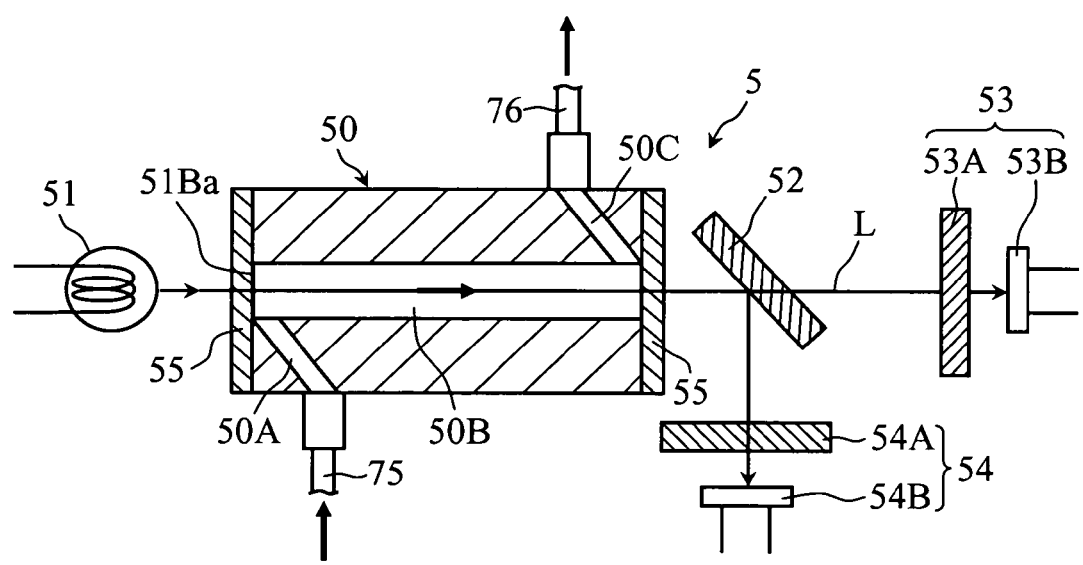
FIG. 2 is a cross-sectional view for describing a photometry mechanism in the HPLC apparatus shown in FIG. 1.

As shown in FIG. 2, the photometry mechanism 5 optically detects hemoglobin contained in an eluent from the analytical column 40 and has a photometry cell 50, a light source 51, a beam splitter 52, a light receiving system 53 for measurement and a receiving system 54 for reference.

The photometry cell 50 defines the photometry area. This photometry cell 50 has an introduction path 50A and a photometry path 50B and a discharge path 50C, and these paths 50A, 50B, 50C are communicated in series. The introduction path 50A introduces an eluent from the analytical column 40 (see FIG. 1) into the photometry path 50B, and is connected to the analytical column 40 through piping 75. The photometry path 50B provides a place for flowing of an eluent to be a photometry target and for photometry of an eluent and is formed in a linear fashion. This photometry path 50B has both ends open, and its both ends are closed by a transparent cover 55. The discharge path 50C discharges an eluent of the photometry path 50B, and is connected to the waste fluid bath 15 through piping 76 (see FIG. 1).

The light source 51 irradiates an eluent flowing through the photometry path 50B with light. This light source 51 is arranged facing an end face 50Ba of the photometry path 50B (transparent cover 55) so that the optic axis L may pass the center of the photometry path SOB. A light source 51 that can be used and eject light of a measurement wavelength and a reference wavelength in which the molecular extinction coefficient of oxyhemoglobin agrees or substantially agrees with that of deoxyhemoglobin. The measurement wavelengths can include, for example, the wavelength range of 417 to 426 nm and may be from 520 to 526 nm or from 583 to 589 nm. The reference wavelength can adopt, for example, 500 nm. The light sources 51 that can be used and eject light of the measurement and reference wavelengths of the previous wavelength range include halogen lamps. As a matter of fact, means other than a halogen lamp, for example, means including one or a plurality of LED elements can be also used as the light source 51.

The beam splitter 52 divides light passing through the photometry path 50B among light going out of the light source 51 and makes the light enter the light receiving system 53 for measurement and the light receiving system 54 for reference. The splitter is placed at an inclination angle of 45 degrees on the optic axis L. Well-known, various apparatuses such as a semi-transparent mirror can be used as the beam splitter 52.

The light receiving system 53 for measurement selectively receives light of a target wavelength among light permeating the beam splitter 52 and is placed on the optic axis L. This light receiving system 53 for measurement includes an interference filter 53A and a light receiving element 53B for receiving light permeating the interference filter 53A. A photodiode can be used as the light receiving element 53B.

Figure 3:
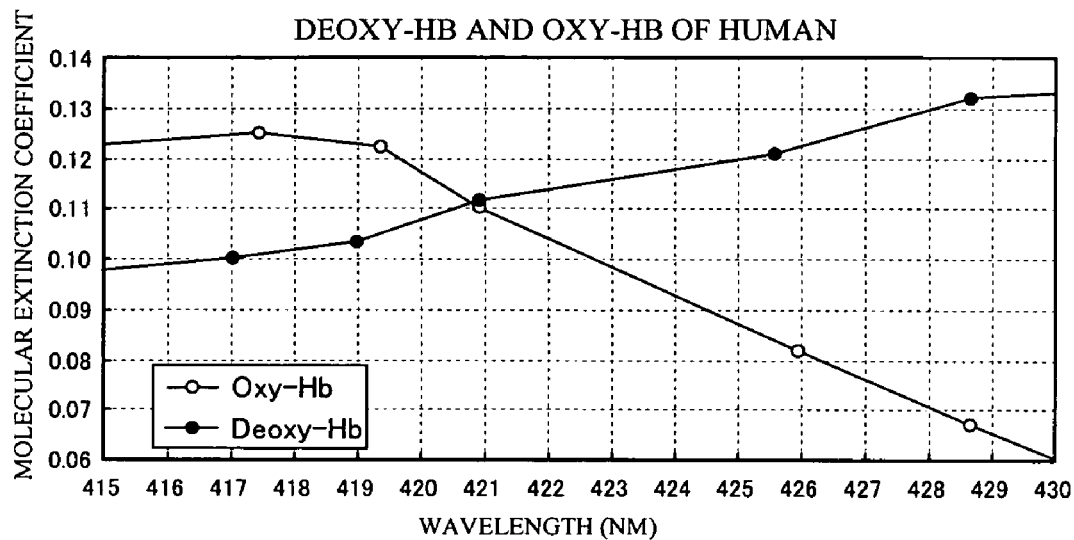
FIG. 3 is a graph indicating of the wavelength dependency of the molecular extinction coefficient of oxyhemoglobin and deoxyhemoglobin.

The interference filter 53A selectively permeates the light of a target measurement wavelength. Here, in an HPLC apparatus X, the measurement wavelength is set at from 417 to 426 nm and preferably at from 419 to 423 nm. This is due to the following reasons. First, this seems to be because, as shown in FIG. 3, the molecular extinction coefficient of oxyhemoglobin agrees with the molecular extinction coefficient of deoxyhemoglobin at a wavelength of about 421 nm, whereby the concentration of hemoglobin can be measured without being affected by the ratio of amounts of oxyhemoglobin and deoxyhemoglobin or its variation in the hemoglobin contained in an eluent from the analytical column 40, if the measurement wavelength is 421 nm or a wavelength close to it. Secondly, it seems to be because, as clarified in an example below, the result is obtained that the least influence of the environmental temperature is received when the measurement wavelength is 423 nm, so that a precise and stable glycated hemoglobin concentration can be measured without being hardly affected by the environmental temperature, if the measurement wavelength is 423 nm or close to it.

The measurement wavelength can adopt 520 to 526 nm or 583 to 589 nm in which, as described above, the molecular extinction coefficient of oxyhemoglobin agrees or substantially agrees with the molecular extinction coefficient of deoxyhemoglobin. Hence, in this case, the interference filter 53A is used that makes light in the wavelength range of 520 to 526 nm or 583 to 589 nm be selectively permeated.

The light receiving system 54 for reference illustrated in FIG. 2 acquires data for suppressing the influence of the turbidity and scattering of an eluent from the analytical column 40 and selectively receives light of a reference wavelength of 500 nm among light the optical path of which is altered by reflection in the beam splitter 52. This light receiving system 74 for measurement includes the interference filter 54A that selectively permeates light of 500 nm and the light receiving element 54B for receiving light permeating the interference filter 54A. A photodiode can be used as the light receiving element 54B.

Figure 4:
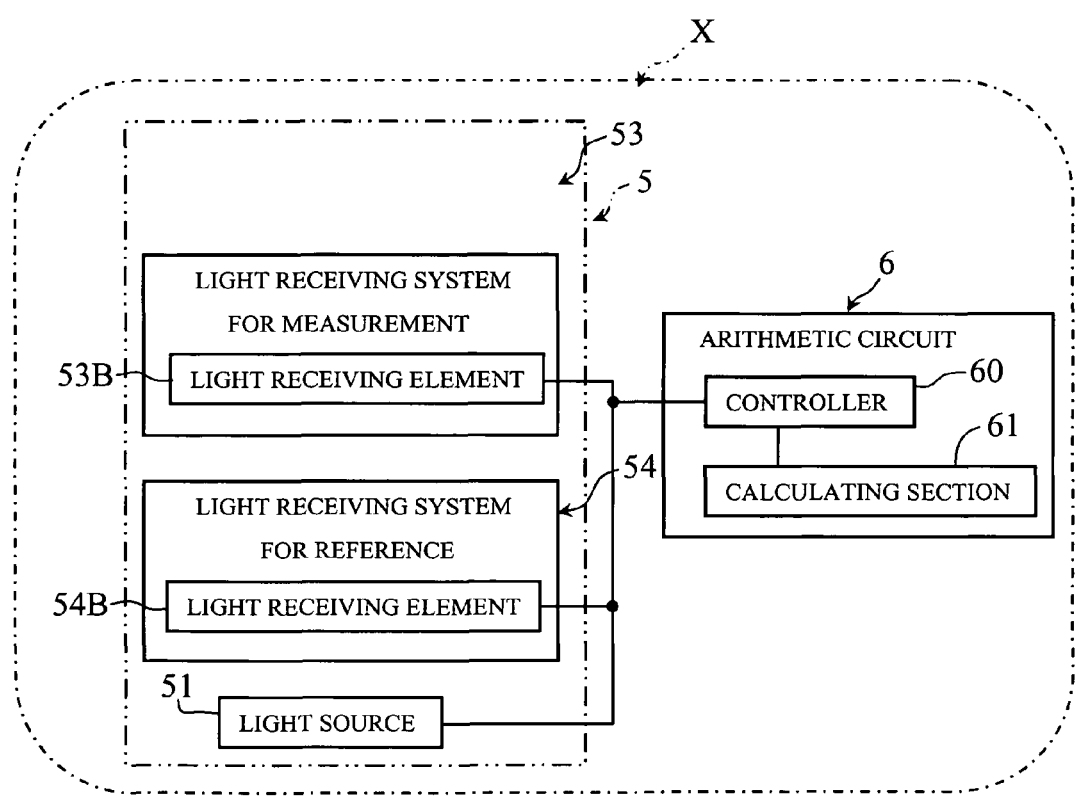
FIG. 4 is block diagram showing the main part of the HPLC apparatus shown in FIG. 1.

As shown in FIG. 4, the arithmetic circuit 6 includes a controller 60 and a calculating section 61.

The controller 60 controls the operation of each section. More specifically, the controller 60 controls the lighting and extinction of the light source 51, controls the interference filter 53A to select a wavelength of light received in the light receiving element 53B, or controls concentration arithmetic processing in the calculating section 61.

The calculating section 61 calculates the concentration of glycated hemoglobin in whole blood based on light reception results in the light receiving elements 53B, 54B. This calculating section 61 memorizes a program necessary for calculation and its operation is controlled by the controller 60.

Next, the operation of the HPLC apparatus X will be described with reference to the flow chart illustrated in FIGS. 5 and 6 in addition to FIGS. 1 to 4.

Figure 5:
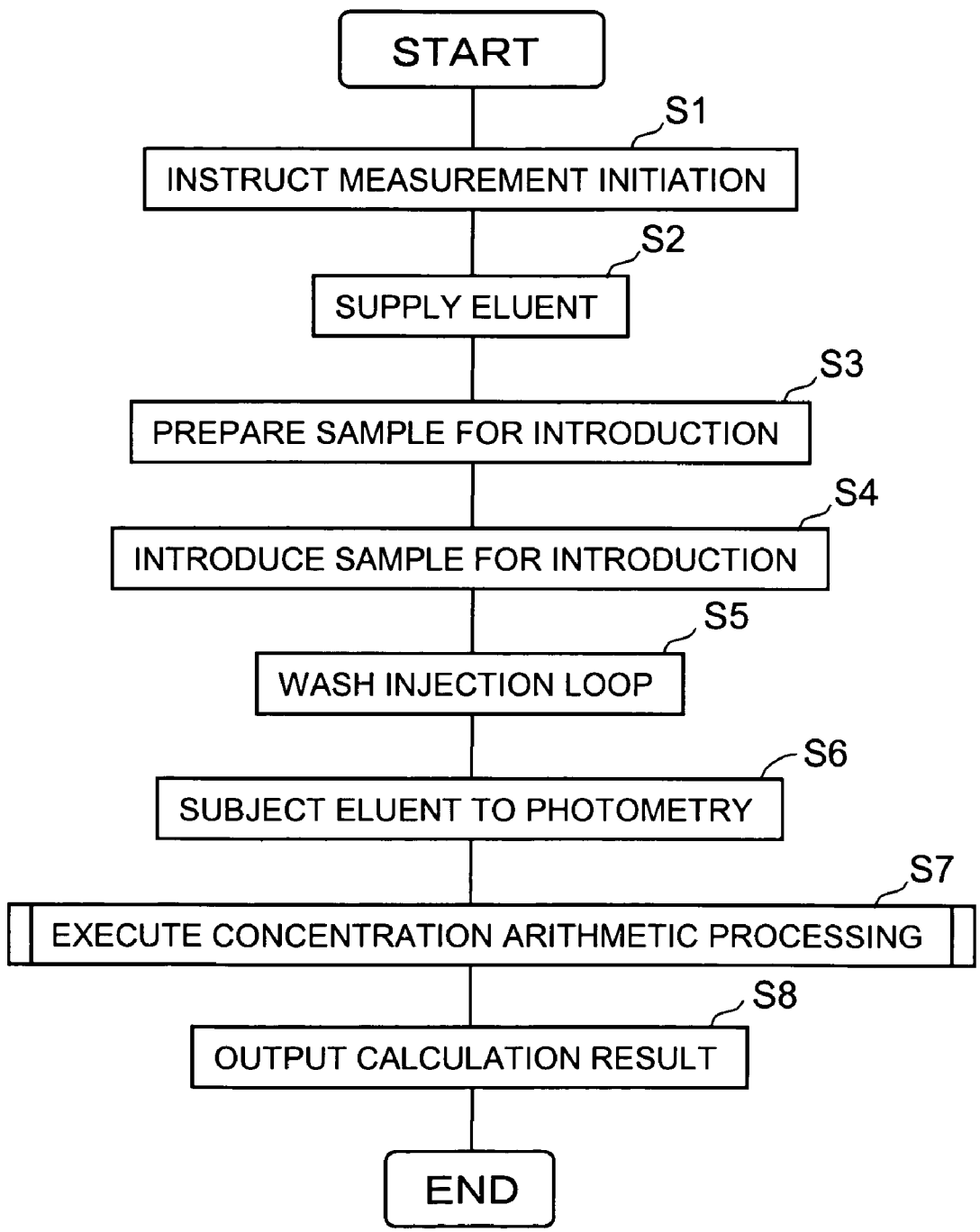
FIG. 5 is a flow chart for describing the operation of the HPLC apparatus shown in FIG. 1.
Figure 6:
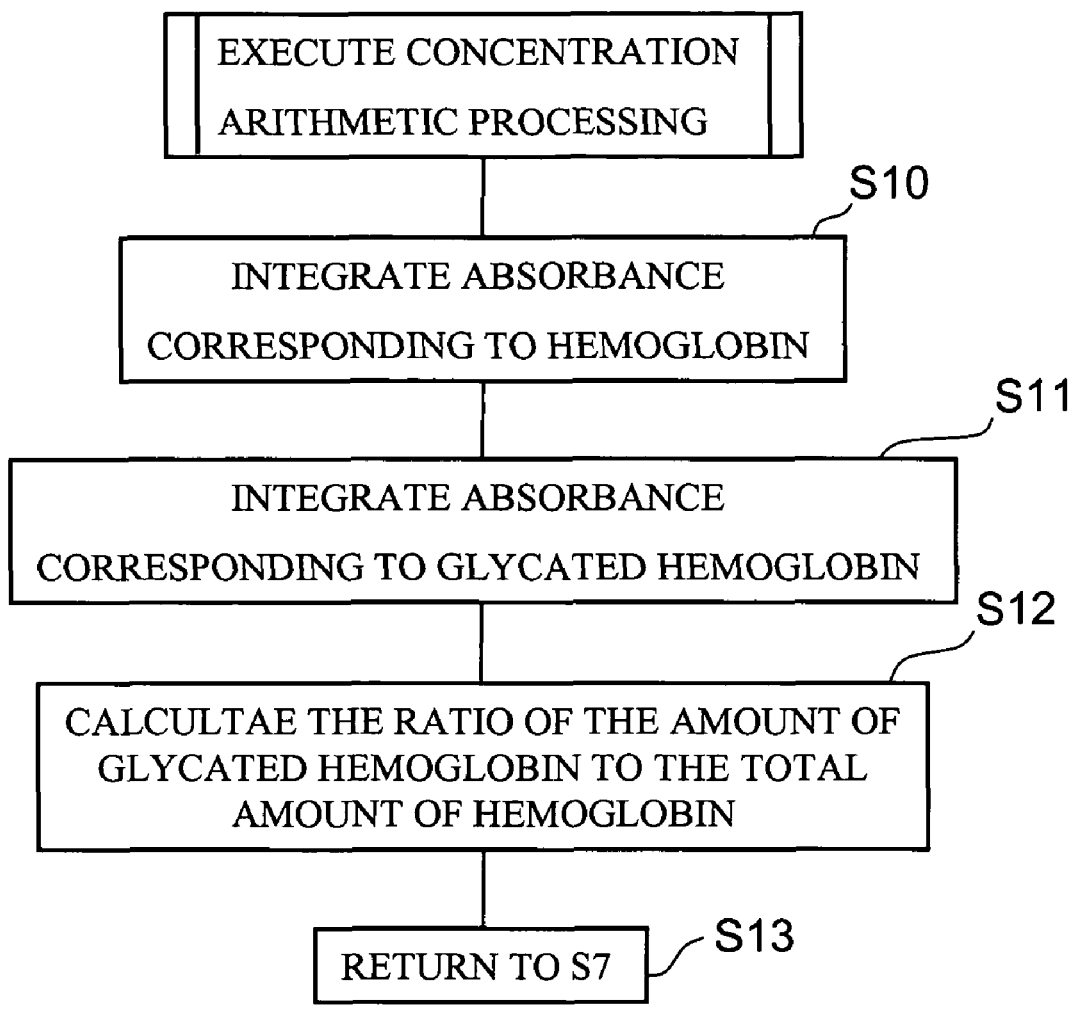
FIG. 6 is a flow chart for describing concentration arithmetic processing in an arithmetic circuit in the HPLC apparatus shown in FIG. 1.

As illustrated in FIGS. 1 and 5, in the HPLC apparatus X, when the instruction of measurement initiation is confirmed (S1), an eluent is supplied to the analytical column 40 (S2). The eluent is supplied from the eluent bottles 10, 11, 12 to the injection valve 43 by the power of the liquid feed pump 42 through the deaerator 2 and the manifold 41. Moreover, from which eluent bottles 10, 11, and 12 among a plurality of eluent bottles 10, 11, and 12 the eluent is supplied is selected by control of the manifold 41. An eluent supplied to the injection valve 43 is supplied to the analytical column 40 through piping 74.

The HPLC apparatus X further prepares a sample for introduction that should be introduced into the analytical column 40 (S3). Upon preparation of a sample for introduction, first, the blood sample 14 is collected from the blood collection tube 13.

The sampling nozzle 30 is operated to collect the blood sample 14 from the blood collection tube 13. The sampling nozzle 30 is operated to supply the blood sample 14 collected by the sampling nozzle 30 to the dilution bath 32. A hemolytic agent and a diluting fluid are further sequentially supplied to the dilution bath 32 from the preparation tank 31, and pipetting operation making use of the sampling nozzle 30 mixes the liquid within the dilution bath 32 to thereby prepare a sample for introduction.

The sample for introduction is introduced into the analytical column 40 (S4). The introduction of a sample for introduction into the analytical column 40 is carried out by executing switch operation of the injection valve 43 and allowing an eluent to flow in the injection loop 44. In other words, a sample for introduction in the injection valve 44 is introduced into the analytical column 40 with an eluent. In the analytical column 40, the introduction of the sample for introduction leads to adsorption of the glycated hemoglobin onto the filler. After adsorption of the glycated hemoglobin on the filler, the kind of eluent supplied to the analytical column 40 is properly changed using the manifold 41 to elute the glycated hemoglobin adsorbed on the filler.

On the other hand, when a fixed time passes from the introduction initiation of the sample for introduction, the injection valve 43 is switched to thereby continuously supply an eluent to the analytical column 40 and also wash the injection loop 44 (S5). On the other hand, at the same time as washing of the injection loop 44, as described previously, a sample for introduction is prepared using the blood sample 14 of the blood collection tube 13 different from the previous one (S3). After washing of the injection loop 44, a sample for introduction is introduced into the injection loop 44 again (S4). Such preparation (S3), introduction (S4) and washing (S5) of a sample for introduction are repeated depending on the number of blood collection tubes 13 (blood samples 14) to be measurement targets while the injection valves 43 are switched properly.

An eluent including glycated hemoglobin discharged from the analytical column 40, as shown in FIG. 2, is supplied to the photometry cell 50 of the photometry mechanism 5 through piping 76 and then subjected to photometry (S6). An eluent from the analytical column 40 is introduced into the photometry cell 50 through piping 75 and the introduction path 50A. This eluent passes through the photometry path 50B and the discharge path 50C and then is led into the waste fluid bath 15 through piping 76, as shown in FIG. 2.

As illustrated in FIG. 2, in the photometry mechanism 5, an eluent from the analytical column 40, when passing through the photometry path 50B, is continuously irradiated with light by the light source 51. On the other hand, the light that passes through the photometry path 50B is divided in the beam splitter 52 and then receives light in the light receiving system 53 for measurement and the light receiving system 54 for reference. In the light receiving system 53 for measurement, light that passes through the interference filter 53A is selectively received in the light receiving element 53B. On the other hand, in the light receiving system 54 for reference, light of 500 nm that is a reference wavelength, passing through the interference filter 54A, is selectively received in the light receiving element 54B.

The light reception results in the light receiving elements 53B, 54B are output to the arithmetic circuit 6, and the concentration of the glycated hemoglobin is calculated in this arithmetic circuit 6 (S7). Concentration arithmetic processing in the arithmetic circuit 6 is executed according to the procedure of the flow chart shown in FIG. 6.

Figure 7:
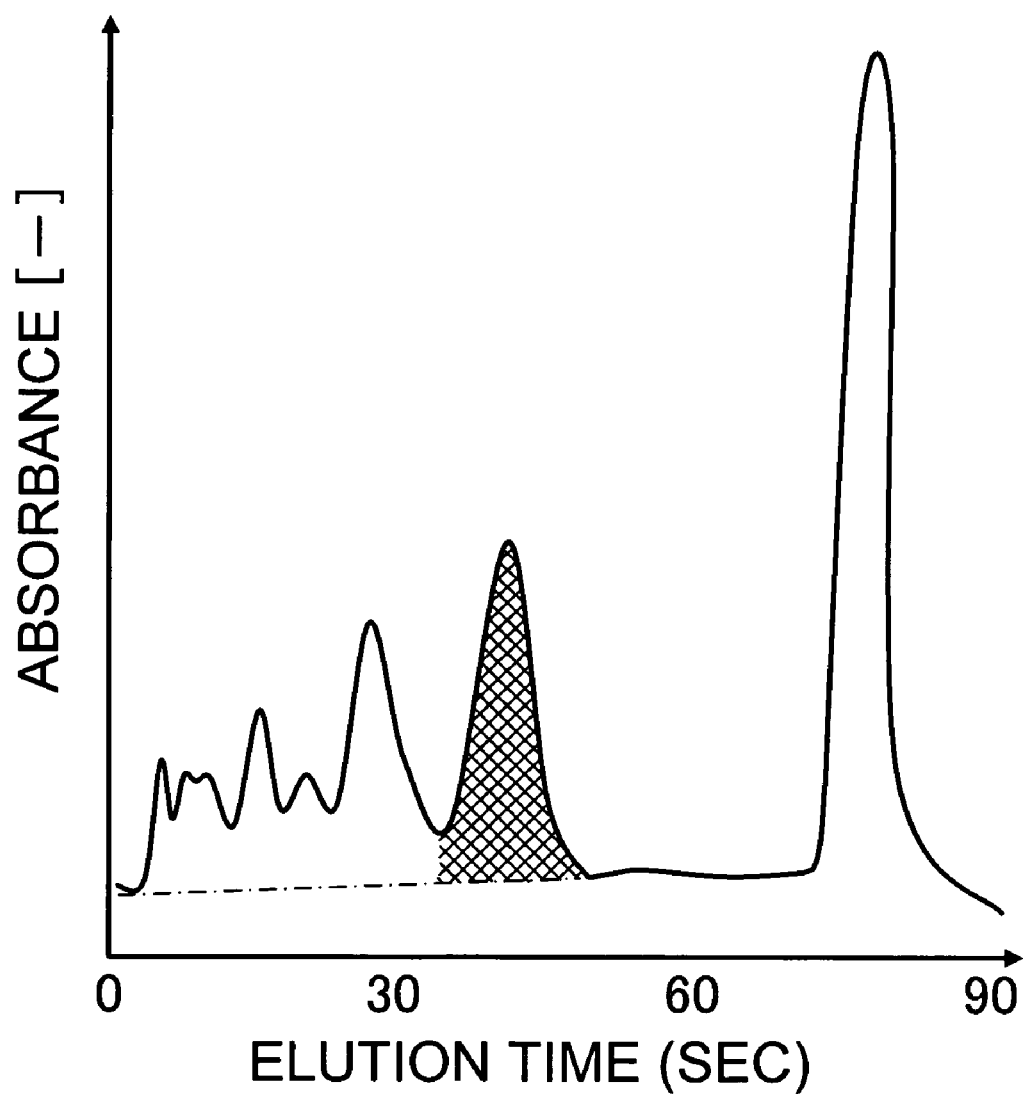
FIG. 7 is one example of a chromatogram obtained in the HPLC apparatus shown in FIG. 1.
Figure 10:
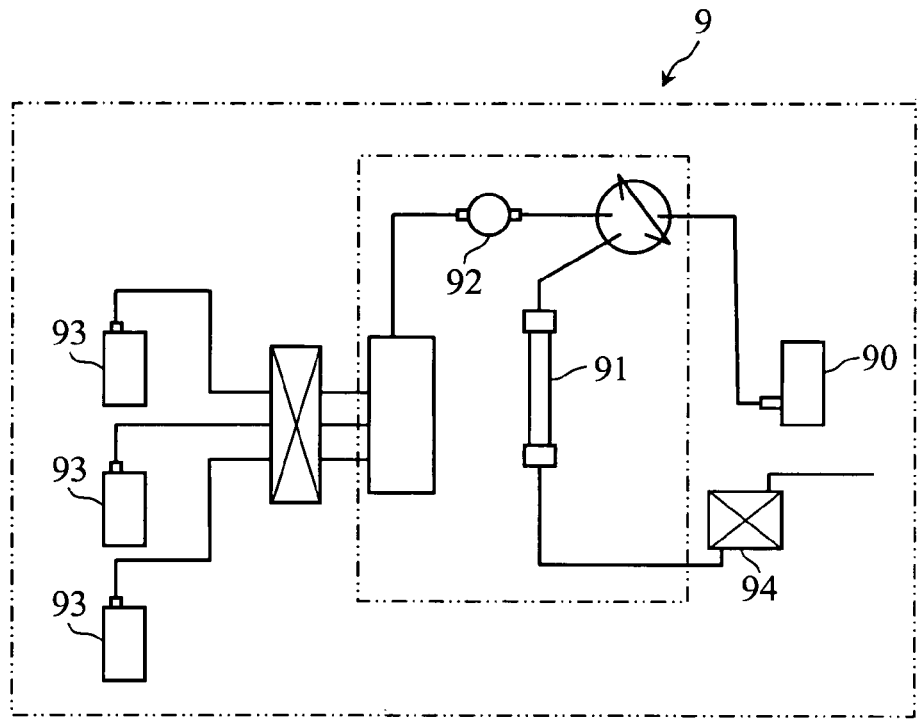
FIG. 10 is a schematic block diagram showing an HPLC apparatus that is one example of a conventional glycated hemoglobin measuring apparatus.
Figure 11:
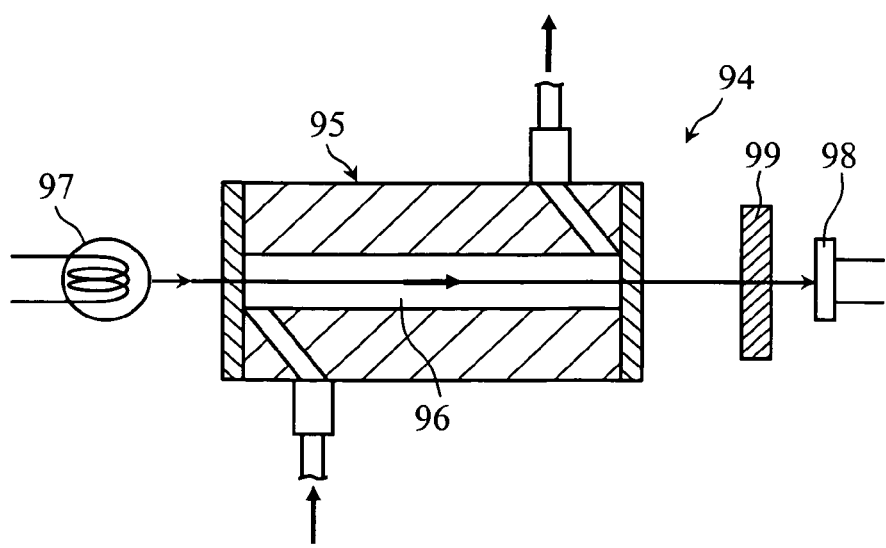
FIG. 11 is a cross-sectional view for describing a photometry mechanism in the HPLC apparatus shown in FIG. 10.

First, the absorbance corresponding to the hemoglobin is integrated (S10) and the absorbance corresponding to the glycated hemoglobin (part shown by cross hatching in FIG. 7) is integrated (S11).

Next, the proportion of the integrated value in S11 to the integrated value of absorbance in S10 is calculated and is taken as the concentration of the glycated hemoglobin (S12).

When the calculation in S12 is completed, the operation is returned to S7 in FIG. 5 (S13). That is, the calculation result in the arithmetic circuit 6 is displayed in a display panel (not illustrated) and printed out automatically or by a user's button operation (S8).

In this embodiment, a wavelength in which the molecular extinction coefficient of oxyhemoglobin agrees or substantially agrees with the molecular extinction coefficient of deoxyhemoglobin is taken as the measurement wavelength and the concentration of glycated hemoglobin is calculated. A wavelength in which the molecular extinction coefficient of oxyhemoglobin agrees with the molecular extinction coefficient of deoxyhemoglobin is constant without being affected by the ratio of the amounts of oxyhemoglobin and deoxyhemoglobin. When the concentration of glycated hemoglobin is calculated in such a wavelength, a stable measurement becomes possible regardless of the ratio of the amounts of oxyhemoglobin and deoxyhemoglobin. As a result, in this embodiment, when the concentration of glycated hemoglobin is measured in an environment in which the temperature outside the HPLC apparatus X (environmental temperature) varies or in states in which the environmental temperatures are different, or even when the variation of the oxygen concentration in a sample to be introduced into an analytical column is caused, the glycated hemoglobin concentration can be stably determined regardless of the ratio of the amounts of oxyhemoglobin and deoxyhemoglobin in an eluent.

The present invention is not limited to the embodiment previously described, and can be changed to various embodiments. For example, in the concentration arithmetic processing previously described, although the amount of hemoglobin is acquired as absorbance, it is not necessarily as absorbance. The amount of hemoglobin may be acquired as transmissivity or simply as the amount of light received.

In addition, in the photometry mechanism 5, a construction in which light of a target wavelength (e.g., light of the wavelength range of 417 to 426 nm) is made received in the light receiving element 53B is not limited by a construction using the interference filter 53A and other well-known techniques can also be adopted.

The present invention is not limited to an HPLC apparatus for measuring the concentration of glycated hemoglobin in blood and can also be further applied to a case of using a specimen other than blood or to a liquid chromatography apparatus other than an HPLC apparatus or to other apparatus of measuring the concentration of glycated hemoglobin.

EXAMPLE 1

In this example, the effects of the measurement wavelength on measurements of glycated hemoglobin as well as the relationship between the environmental temperature and the measurement wavelength were studied.

The concentration of glycated hemoglobin was determined at environmental temperatures of 10° C., 20° C., and 30° C. by adopting as a light receiving element a photodiode array ("UV-visible multi-wavelength detector MD-910"; manufactured by Jasco Co.) using a glycated hemoglobin measuring apparatus ("ADAMS A1c HA-8160"; manufactured by Arkray, Inc.). The concentration of the glycated hemoglobin was calculated as the proportion occupied by the amount of the glycated hemoglobin in the total amount of hemoglobin per 1 nm in the wavelength range of 415 to 430 nm.

Blood (diabetic patient blood) collected from a healthy individual and blood collected from a diabetic patient (diabetic patient blood) were used as specimens. The measurement results of glycated hemoglobin when healthy individual specimens were used are shown in Table 1 and FIG. 8A below and the measurement results of glycated hemoglobin when diabetic patient specimens were used are shown in Table 2 and FIG. 8B below.

TABLE 1

Healthy individual specimen

| Measurement wavelength | Measurements of glycated hemoglobin concentration | | |
|---|---|---|---|
| | 10° C. | 20° C. | 40° C. |
| 415 | 4.33 | 4.73 | 5.10 |
| 416 | 4.45 | 4.63 | 5.09 |
| 417 | 4.45 | 4.69 | 5.07 |
| 418 | 4.30 | 4.65 | 5.07 |
| 419 | 4.45 | 4.68 | 5.03 |
| 420 | 4.44 | 4.76 | 4.72 |

TABLE 1-continued

Healthy individual specimen

| Measurement wavelength | Measurements of glycated hemoglobin concentration | | |
|---|---|---|---|
| | 10° C. | 20° C. | 40° C. |
| 421 | 4.44 | 4.56 | 4.76 |
| 422 | 4.37 | 4.57 | 4.75 |
| 423 | 4.42 | 4.51 | 4.44 |
| 424 | 4.52 | 4.44 | 4.11 |
| 425 | 4.31 | 4.40 | 4.08 |
| 426 | 4.41 | 4.40 | 4.01 |
| 427 | 4.39 | 4.29 | 3.79 |
| 428 | 4.39 | 4.14 | 3.69 |
| 429 | 4.38 | 3.94 | 3.54 |
| 430 | 4.60 | 3.80 | 3.19 |

TABLE 2

Diabetic patient specimen

| Measurement wavelength | Measurements of glycated hemoglobin concentration | | |
|---|---|---|---|
| | 10° C. | 20° C. | 40° C. |
| 415 | 8.41 | 8.83 | 9.68 |
| 416 | 8.41 | 8.95 | 9.78 |
| 417 | 8.25 | 9.13 | 9.50 |
| 418 | 8.44 | 9.00 | 9.42 |
| 419 | 8.53 | 8.92 | 9.14 |
| 420 | 8.38 | 8.79 | 9.16 |
| 421 | 8.55 | 8.59 | 8.97 |
| 422 | 8.42 | 8.49 | 8.96 |
| 423 | 8.52 | 8.53 | 8.52 |
| 424 | 8.49 | 8.29 | 8.00 |
| 425 | 8.39 | 8.20 | 7.88 |
| 426 | 8.37 | 8.24 | 7.52 |
| 427 | 8.36 | 7.86 | 7.34 |
| 428 | 8.29 | 7.60 | 6.78 |
| 429 | 8.26 | 7.39 | 6.62 |
| 430 | 8.23 | 7.12 | 6.15 |

For the healthy individual specimens, Table 1 and FIG. 8A show that the measurements were substantially the same regardless of the environmental temperature when the measurement wavelength was 423 nm. In addition, when the measurement wavelength was in the range of from 416 to 427 nm, the measurement wavelength was the maximum absorption wavelength of oxyhemoglobin. The measurements were constant without being affected by the environmental temperature as compared with the case where the wavelength was 415 nm. In particular, the measurements were not further less affected by the environmental temperature when the measurement wavelength was 419 to 426 nm.

On the other hand, also for the diabetic patient specimens, Table 2 and FIG. 8B show that the measurements were substantially the same regardless of the environmental temperature when the measurement wavelength was 423 nm. Additionally, when the measurement wavelength was in the range of from 417 to 427 nm, the measurement wavelength was the maximum absorption wavelength of oxyhemoglobin. The measurements were constant without being affected by the environmental temperature as compared with the case where the wavelength was 415 nm. In particular, the measurements were not further less affected by the environmental temperature when the measurement wavelength was 419 to 425 nm.

The results of this Example show that, where the glycated hemoglobin concentration is measured, when the measurement wavelength is set at from 417 to 427 nm, preferably from 419 to 425 nm, most preferably 423 nm, the measurement can be precisely and stably carried out with being hardly affected by the environmental temperature regardless of healthy individual specimens or diabetic patient specimens.

EXAMPLE 2

In this example, when the measurement wavelength was set at 415 nm that is the maximum absorption wavelength of oxyhemoglobin and when the measurement wavelength was set at 423 nm that provided the best results in Example 1, the effects of the environmental temperature on the measurements were studied.

Measurements of glycated hemoglobin was measured as in Example 1 on each healthy individual specimen and each diabetic patient specimen. The measurement results when the measurement wavelength was set at 415 nm are shown in Table 3 and FIG. 9A below and the measurement results when the measurement wavelength was set at 423 nm are shown in Table 4 and FIG. 9B below.

TABLE 3

Measurement wavelength 415 nm

| | Measurements of glycated hemoglobin concentration | | |
|---|---|---|---|
| | 10° C. | 20° C. | 30° C. |
| Healthy individual specimen | 4.33% | 4.73% | 5.10% |
| Diabetic patient specimen | 8.41% | 8.83% | 9.68% |

TABLE 4

Measurement wavelength 423 nm

| | Measurements of glycated hemoglobin concentration | | |
|---|---|---|---|
| | 10° C. | 20° C. | 30° C. |
| Healthy individual specimen | 4.42% | 4.51% | 4.44% |
| Diabetic patient specimen | 8.52% | 8.53% | 8.52% |

As shown in Table 3 and FIG. 9A, when the measurement wavelength was set at 415 nm that is the maximum absorption wavelength of oxyhemoglobin and the glycated hemoglobin was measured, the measurement was increased with increasing environmental temperature and was greatly affected by the environmental temperature.

On the other hand, as shown in Table 4 and FIG. 9B, when the measurement wavelength was set at 423 nm and the glycated hemoglobin concentration was calculated, the measurement was hardly affected by the environmental temperature and was substantially constant, even if the environmental temperature was changed in the range of from 10 to 30° C. In particular, in the diabetic patient specimens, measurements that require more precise measurement hardly varied to the environmental temperature. This shows that, when the measurement wavelength is set at 423 nm and the glycated hemoglobin concentration is calculated, the measurement of the glycated hemoglobin concentration is not affected by the environmental temperature (dissolved oxygen concentration of an eluent) and the dissolved oxygen concentration of a sample, and a precise and stable measurement of the glycated hemoglobin concentration is possible. In addition, it is estimated that, even when the measurement wavelength is set close to a wavelength of 423 nm, the measurement is hardly affected by the environmental temperature and a precise and stable measurement of the glycated hemoglobin concentration is possible.

Consequently, it has been shown that the selection of a wavelength close to 423 nm makes it possible to precisely measure the concentration of glycated hemoglobin regardless of the ratio of the amounts of oxyhemoglobin and deoxyhemoglobin.

The invention claimed is:

1. A method of measuring the concentration of glycated hemoglobin in a sample, the method comprising the steps of:
    irradiating the sample with light of a measurement wavelength, the measurement wavelength being set at about 423 nm,
    irradiating the sample with light of a reference wavelength, and
    calculating the concentration of glycated hemoglobin in the sample based on reception results of the measurement wavelength and correction data, the correction data being based on reception results of the reference wavelength.

2. The method of measuring the concentration of glycated hemoglobin according to claim 1, further comprising:
    separating glycated hemoglobin by column chromatography so as to prepare the sample.

3. The method of measuring the concentration of glycated hemoglobin according to claim 2, further comprising:
    preparing laked blood from red blood cells prior to the separating of the glycated hemoglobin.

4. The method of measuring the concentration of glycated hemoglobin according to claim 1, further comprising:
    dividing light that travels through the sample into light of the measurement wavelength and light of the reference wavelength.

5. The method of measuring the concentration of glycated hemoglobin according to claim 4, further comprising:
    receiving the light of the measurement wavelength that travels through the sample with a first light receiving section.

6. The method of measuring the concentration of glycated hemoglobin according to claim 5, further comprising:
    receiving the light of the reference wavelength that travels through the sample with a second light receiving section.

7. An apparatus configured to measure the concentration of glycated hemoglobin, the apparatus comprising:
    a photometry mechanism in which a sample is irradiated with light of a measurement wavelength, the measurement wavelength being set at about 423 nm, and light from a reference wavelength, wherein the photometry mechanism includes
        a first light receiving section that receives light of the measurement wavelength that travels through the sample, and
        a second light receiving section that receives light of the reference wavelength that travels through the sample; and
    a calculating section that calculates the concentration of glycated hemoglobin in the sample based on reception results of the measurement wavelength and correction data, the correction data being based on reception results of the reference wavelength.

8. The apparatus according to claim 7, further comprising:
    a separation unit configured to separate glycated hemoglobin by column chromatography so as to prepare the sample.

9. The apparatus according to claim 8, further comprising:
    a sample preparation mechanism configured to prepare laked blood from red blood cells prior to separation of the glycated hemoglobin.

10. The apparatus according to claim 7, further comprising:
    a beam splitter that divides the light of the measurement wavelength that travels through the sample from the light of the reference wavelength that travels through the sample.

11. The apparatus according to claim 7, wherein the second light receiving section is configured to receive light of the reference wavelength of about 500 nm.

* * * * *